US009328055B2

(12) United States Patent
Balakrishnan et al.

(10) Patent No.: US 9,328,055 B2
(45) Date of Patent: May 3, 2016

(54) SYSTEMS AND METHODS OF REFINING NATURAL OIL FEEDSTOCKS AND DERIVATIVES THEREOF

(71) Applicant: Elevance Renewable Sciences, Inc., Woodridge, IL (US)

(72) Inventors: Chander Balakrishnan, Woodridge, IL (US); Yenamandra Viswanath, Woodridge, IL (US); Efimia Metsi-Guckel, Woodridge, IL (US); Mary Bjorklund, Woodridge, IL (US); Yongyou Hu, Woodridge, IL (US); Jason Bronkema, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/658,401

(22) Filed: Mar. 16, 2015

(65) Prior Publication Data

US 2015/0266802 A1   Sep. 24, 2015

Related U.S. Application Data

(60) Provisional application No. 61/955,711, filed on Mar. 19, 2014.

(51) Int. Cl.
| | |
|---|---|
| *C07C 67/00* | (2006.01) |
| *C07C 67/56* | (2006.01) |
| *C07C 67/03* | (2006.01) |
| *C07C 67/333* | (2006.01) |

(52) U.S. Cl.
CPC ............... *C07C 67/56* (2013.01); *C07C 67/03* (2013.01); *C07C 67/333* (2013.01)

(58) Field of Classification Search
CPC ........ C07C 67/56; C07C 67/03; C07C 67/333
USPC ......................................................... 554/124
See application file for complete search history.

(56) References Cited

U.S. PATENT DOCUMENTS

| | | | |
|---|---|---|---|
| 7,576,227 B2 | 8/2009 | Lysenko et al. | |
| 8,614,344 B2 | 12/2013 | Kaido et al. | |
| 2011/0113679 A1 | 5/2011 | Cohen et al. | |
| 2013/0217906 A1 | 8/2013 | Kunz et al. | |

FOREIGN PATENT DOCUMENTS

WO    2008/048522    4/2008

OTHER PUBLICATIONS

MOL, Topics in Catalysis, vol. 27, pp. 97-104 (2004).
VOOGT, Biotech. Biooeng., vol. 92(5), pp. 532-540 (2005).
International Search Report, PCT App. No. PCT/US2015/020647.

*Primary Examiner* — Deborah D Carr
(74) *Attorney, Agent, or Firm* — Robert S. Dailey (57) ABSTRACT

Systems and methods are disclosed for refining natural oil feedstocks. In some embodiments, the methods comprise transesterifying glycerides in a natural oil feedstock to provide a transesterified product comprising monounsaturated fatty acid esters and polyunsaturated fatty acid esters. In some embodiments, the methods comprise separating the polyunsaturated fatty acid esters from the monounsaturated fatty acid esters (or vice versa), to provide a separated monounsaturated fatty acid ester composition having a ratio of at least 10 parts by weight of monounsaturated fatty acid esters for every 1 part by weight of polyunsaturated fatty acid esters.

20 Claims, 4 Drawing Sheets

SYSTEMS AND METHODS OF REFINING NATURAL OIL FEEDSTOCKS AND DERIVATIVES THEREOF

CROSS-REFERENCE TO RELATED APPLICATIONS

The present application claims the benefit of priority of U.S. Provisional Application No. 61/955,711, filed Mar. 19, 2014, which is hereby incorporated by reference as though fully set forth herein in its entirety.

TECHNICAL FIELD

Systems and methods of refining natural oil feedstocks and derivatives thereof are disclosed. In particular, systems and methods of separating polyunsaturated fatty acid esters from monounsaturated fatty acid esters are disclosed. The separated polyunsaturated fatty acid esters and separated monounsaturated fatty acid esters are further processed by metathesis in a biorefinery system.

BACKGROUND

In recent years, there has been an increased demand for environmentally friendly techniques for manufacturing materials derived from non-petroleum sources. For example, researchers have been studying the feasibility of manufacturing biofuels, waxes, plastics, lubricants, polymers, and the like, using natural oil feedstocks, such as vegetable and seed-based oils. Metathesis reactions involving natural oil feedstocks offer promising solutions for today and for the future.

Natural oil feedstocks of interest include non-limiting examples such as natural oils (e.g., vegetable oils, fish oil, animal fats) and derivatives of natural oils, such as fatty acids and fatty acid alkyl (e.g., methyl) esters. These feedstocks may be converted into industrially useful chemicals (e.g., waxes, plastics, cosmetics, biofuels, etc.) by any number of different reaction mechanisms, including metathesis reaction mechanisms. Significant reaction classes include, as non-limiting examples, self-metathesis, cross-metathesis with olefins, and ring-opening metathesis reactions.

Depending on the level of unsaturation in the natural oil feedstock, esters and olefins produced from the refining process typically include levels of polyunsaturated components, potentially decreasing their market value or requiring additional processing (e.g., capital and operating costs) to upgrade their values. Additionally, the polyunsaturation in the oil may cause the formation of cyclohexadiene (CHD), which may lead to undesired levels of benzene, or the loss of desirable olefin products based on downstream separation processes. Therefore, it is desirable to improve the efficiency of the refining processes, and the reaction mechanisms and separation processes associated therewith.

SUMMARY

Systems and methods are provided for refining natural oil feedstocks and derivatives thereof. In one aspect, the method comprises providing a natural oil feedstock comprising glycerides. The method further comprises transesterifying glycerides in a natural oil feedstock to provide a transesterified product comprising monounsaturated fatty acid esters and polyunsaturated fatty acid esters. The method further comprises separating the polyunsaturated fatty acid esters from the monounsaturated fatty acid esters, to provide a separated monounsaturated fatty acid ester composition having a ratio of at least 10 parts by weight of monounsaturated fatty acid esters for every 1 part by weight of polyunsaturated fatty acid esters. The method further comprises metathesizing the separated monounsaturated fatty acid ester composition in the presence of a metathesis catalyst to provide a metathesized product comprising metathesized monounsaturated fatty acid esters and at least one olefin.

BRIEF DESCRIPTION OF THE DRAWINGS

The following drawings are provided to illustrate certain embodiments described herein. The drawings are merely illustrative, and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Separation of Polyunsaturates and Monounsaturates

In certain aspects, the disclosure provides methods for separating (a) polyunsaturated fatty acid esters and (b) monounsaturated fatty acid esters. The methods include introducing a fatty acid ester feedstock comprising polyunsaturated fatty acid esters and monounsaturated fatty acid esters into a separation unit or separation process. In certain embodiments, the feedstock additionally comprises saturated fatty acid esters, which may be additionally processed and separated from the polyunsaturated fatty acid esters and/or monounsaturated fatty acid esters.

Through the separation processes described herein, it is possible to improve the yield or purity of a downstream targeted product stream. The separation process may also allow for an easier optimization for the desired products. For example, as described in greater detail below, improved purity or yield of metathesized products (e.g., 9-decenoic acid methyl ester or 9-decenoic acid) are available following separation of the polyunsaturated fatty acid esters. Additionally, the separation processes described herein may allow for a more economical processing system having fewer separation columns to separate the various intermediates or final products.

The separation process may comprise an actual or simulated moving bed chromatographic process, a crystallization process, a membrane process, a distillation process, a salt solubility process, an adsorption process, a phase separation process, an ionic liquid separation process, a urea complexation process, or a combination thereof. Certain separation processes are described in U.S. Pat. No. 8,173,826, herein incorporated by reference in its entirety.

Through one or more of the separation processes, a separation of the polyunsaturated fatty acid esters and the monounsaturated fatty acid esters (and, optionally, saturated fatty acid esters) may be achieved. In certain embodiments, polyunsaturated fatty acid esters and monounsaturated fatty acid esters are separated to provide a separated monounsaturated fatty acid ester composition having a ratio of at least 10 parts by weight of monounsaturated fatty acid esters for every 1 part by weight of the polyunsaturated fatty acid esters. That is, the ratio of monounsaturated fatty acid esters to polyunsaturated fatty acid esters in the separated monounsaturated fatty acid ester composition is at least 10:1. In other embodiments, the ratio of monounsaturated fatty acid esters to polyunsaturated fatty acid esters in the monounsaturated fatty acid ester composition is at least 20:1, at least 30:1, at least 40:1, at least 50:1, at least 60:1, at least 70:1, at least 80:1, at least 90:1, or at least 100:1.

In other embodiments, polyunsaturated fatty acid esters and monounsaturated fatty acid esters are separated to provide a separated polyunsaturated fatty acid ester composition having a ratio of at least 10 parts by weight of polyunsaturated fatty acid esters for every 1 part by weight of the monounsaturated fatty acid esters. That is, the ratio of polyunsaturated fatty acid esters to monounsaturated fatty acid esters in the separated polyunsaturated fatty acid ester composition is at least 10:1). In other embodiments, the ratio of polyunsaturated fatty acid esters to monounsaturated fatty acid esters in the polyunsaturated fatty acid ester composition is at least 20:1, at least 30:1, at least 40:1, at least 50:1, at least 60:1, at least 70:1, at least 80:1, at least 90:1, or at least 100:1.

In some embodiments, the separation process removes at least 50 wt. %, at least 60 wt. %, at least 70 wt. %, at least 80 wt. %, at least 90 wt. %, at least 95 wt. %, or at least 99 wt. % of the polyunsaturated fatty acid esters from the remaining fatty acid ester compounds (e.g., saturated fatty acid esters, monounsaturated fatty acid esters) in the fatty acid ester feedstock. In certain embodiments, the separation process forms a composition having a majority of the polyunsaturated fatty acid esters (e.g., at least 50%, at least 60 wt. %, at least 70 wt. %, at least 80 wt. %, at least 90 wt. %, at least 95 wt. %, or at least 99 wt. % of the polyunsaturated fatty acid esters), and a minority of the combined monounsaturated fatty acid esters and saturated fatty acid esters from the fatty acid ester feedstock (e.g., less than 50 wt. %, less than 25 wt. %, less than 20 wt. %, less than 10 wt. %, less than 5 wt. %, or less than 1 wt. % of the combined monounsaturated and saturated fatty acid esters). The separation process additionally may form a second composition having a majority of the combined monounsaturated fatty acid esters and the saturated fatty acid esters from the fatty acid ester feedstock (e.g., at least 50%, at least 60 wt. %, at least 70 wt. %, at least 80 wt. %, at least 90 wt. %, at least 95 wt. %, or at least 99 wt. % of the combined monounsaturated and saturated fatty acid esters), and a minority of the polyunsaturated fatty acid esters (e.g., less than 50 wt. %, less than 25 wt. %, less than 20 wt. %, less than 10 wt. %, less than 5 wt. %, or less than 1 wt. % of the polyunsaturated fatty acid esters).

In one embodiment, the separation process involves separating the polyunsaturated fatty acid esters from the monounsaturated fatty acid esters in a separation unit, to provide a separated polyunsaturated fatty acid esters composition and a separated monounsaturated fatty acid esters composition, wherein (1) the monounsaturated fatty acid ester composition has a ratio of at least 10 parts by weight of monounsaturated fatty acid esters for every 1 part by weight of the polyunsaturated fatty acid esters and (2) the polyunsaturated fatty acid ester composition has a ratio of at least 10 parts by weight of polyunsaturated fatty acid esters for every 1 part by weight of the monounsaturated fatty acid esters.

In certain embodiments, the stream on which the separation is performed comprises monounsaturated fatty acid esters (e.g., alkyl esters, such as methyl, ethyl, isopropyl, and the like, or glyceryl esters) and polyunsaturated fatty acid esters (e.g., alkyl esters, such as methyl, ethyl, isopropyl, and the like, or glyceryl esters). In certain embodiments, the stream also comprises saturated fatty acid esters (e.g., alkyl esters, such as methyl, ethyl, isopropyl, and the like, or glyceryl esters). The monounsaturated fatty acid esters can be esters of any suitable monounsaturated fatty acid, including, but not limited to, oleic acid, vaccenic acid, palmitoleic acid, 9-decenoic acid, 9-dodecenoic acid, and the like. The polyunsaturated fatty acid esters can be esters of any suitable polyunsaturated fatty acid, including, but not limited to, linoleic acid, linolenic acid, 9,12-tridecadienoic acid, 9,12-pentadecadienoic acid, and the like. The saturated fatty acid esters can be esters of any suitable saturated fatty acid, including, but not limited to, stearic, palmitic, and the like. In some embodiments, the stream on which the separation is performed comprises oleic acid esters and linoleic acid esters. In some embodiments, the stream further comprises palmitic acid esters, stearic acid esters, or a combination thereof. In some further embodiments, the stream further comprises linolenic acid esters.

In some embodiments, the certain fatty acid ester components in the stream are separated from the other fatty acid components in the stream. Such a separation can be performed by any of the means described below. In some embodiments, certain fatty acid esters are separated from the stream by adsorbing them using an adsorbent material.

In some embodiments, where the stream comprises both monounsaturated fatty acid esters and polyunsaturated fatty acid esters, the monounsaturated fatty acid esters are selectively separated out (e.g., removed from the stream) relative to the polyunsaturated fatty acid esters. In some embodiments, the weight-to-weight ratio of monounsaturated fatty acid esters removed from the stream to polyunsaturated fatty acid esters removed from the stream is at least 3:1, or at least 4:1, or at least 5:1, or at least 10:1, or at least 20:1, or at least 35:1, or at least 50:1. In some such embodiments, at least 50 percent by weight, or at least 60 percent by weight, or at least 70 percent by weight, or at least 80 percent by weight, or at least 90 percent by weight, of the monounsaturated fatty acid esters are removed from the stream, based on the total weight of monounsaturated fatty acid esters in the stream. In some embodiments, the separating or removing comprises adsorbing the monounsaturated fatty acid esters using an adsorbent.

In some embodiments, where the stream comprises both monounsaturated fatty acid esters and polyunsaturated fatty acid esters, the polyunsaturated fatty acid esters are selectively separated out (e.g., removed from the stream) relative to the monounsaturated fatty acid esters. In some embodiments, the weight-to-weight ratio of polyunsaturated fatty acid esters removed from the stream to monounsaturated fatty acid esters removed from the stream is at least 3:1, or at least 4:1, or at least 5:1, or at least 10:1, or at least 20:1, or at least 35:1, or at least 50:1. In some such embodiments, at least 50 percent by weight, or at least 60 percent by weight, or at least 70 percent by weight, or at least 80 percent by weight, or at least 90 percent by weight, of the polyunsaturated fatty acid esters are removed from the stream, based on the total weight of polyunsaturated fatty acid esters in the stream. In some embodiments, the separating or removing comprises adsorbing the polyunsaturated fatty acid esters using an adsorbent.

Moving Bed Chromatographic Separation

In certain embodiments, the separation process is an actual or simulated moving bed chromatographic separation process. Polyunsaturated fatty acid esters may be removed from the fatty acid ester feedstock through the use of a single actual or simulated moving bed apparatus using an eluent or solvent. In certain embodiments, the eluent is not in a supercritical state. In some embodiments, the eluent is a liquid. Non-limiting examples of actual or simulated moving bed chromatography separation units include those described in U.S. Pat. Nos. 2,985,589; 3,696,107; 3,706,812; 3,761,533; 4,764,276; 5,069,883; and 6,979,402, herein incorporated by reference in their entireties.

The actual or simulated moving bed chromatography unit may include a plurality of linked chromatography columns containing the eluent, where the fatty acid ester feedstock may be separated into an extract stream and a raffinate stream. The raffinate stream may refer to the stream of components that move more rapidly with the liquid eluent phase compared with the solid adsorbent phase, while the extract stream may refer to the stream of components that move more rapidly with the solid adsorbent phase compared with the liquid eluent phase. Thus, the raffinate stream may be enriched with more polar components and depleted of less polar components compared with a feed stream, while the extract stream may be enriched with less polar components and depleted of more polar components as compared with the feed stream.

In certain embodiments, the polyunsaturated fatty acid esters comprise the most polar component of an ester feedstock, and the moving bed chromatography process removes a majority of the polyunsaturated fatty acid esters in the raffinate stream while a majority of the saturated and monounsaturated fatty acid esters are removed in the extract stream. In some embodiments, following separation of the polyunsaturated fatty acid esters, the monounsaturated fatty acid esters are separated from the saturated fatty acid esters. In other embodiments, the moving bed chromatography process removes the saturated fatty acid esters from the polyunsaturated and monounsaturated fatty acid esters. Following this separation, the monounsaturated fatty acid esters may be separated from the polyunsaturated fatty acid esters.

In certain embodiments, the eluent used in the chromatographic separation process is an aqueous alcohol. The aqueous alcohol may include water and one or more short chain alcohols (e.g., alcohols having between 1 and 6 carbon atoms). Examples of suitable alcohols include methanol, ethanol, n-propanol, i-propanol, n-butanol, i-butanol, s-butanol, t-butanol, and combinations thereof. In certain embodiments, the alcohol is methanol and/or ethanol. In one particular embodiment, the alcohol is methanol. In certain embodiments, the water:alcohol ratio of the eluent in the entire apparatus is between 0.1:99.9 and 30:70 parts by volume, between 0.1:99.9 and 9:91 parts by volume, between 0.25:99.75 and 7:93 parts by volume, or between 0.5:99.5 and 6:94 parts by volume.

In other embodiments, the eluent used in the process is an aqueous organic solvent other than aqueous alcohol. As used herein, an "aqueous organic solvent" comprises water and one or more ethers, esters, ketones, nitriles, and combinations thereof. In certain embodiments, the water:organic solvent ratio of the eluent in the entire apparatus is between 0.1:99.9 and 30:70 parts by volume, between 0.1:99.9 and 9:91 parts by volume, between 0.25:99.75 and 7:93 parts by volume, or between 0.5:99.5 and 6:94 parts by volume.

In certain embodiments, the aqueous organic solvent includes an ether solvent. The ether solvent may be a short chain ether having the formula R—O—R', wherein R and R' are the same or different and represent a straight or branched C1-C6 alkyl group. In some embodiments, the C1-C6 alkyl group is unsubstituted. Non-limiting examples of ether solvents include diethylether, diisopropylether, and methyl t-butyl ether (MTBE).

In certain embodiments, the aqueous organic solvent includes an ester solvent. The ester solvent may be a short chain ester having the formula R—(C=O)O—R', wherein R and R' are the same or different and represent a straight or branched C1-C6 alkyl group. Non-limiting examples of ester solvents include methylacetate and ethylacetate.

In certain embodiments, the aqueous organic solvent includes a ketone solvent. The ketone solvent may be a short chain ketone having the formula R—(C=O)—R', wherein R and R' are the same or different and represent a straight or branched C1-C6 alkyl group. In some embodiments, the C1-C6 alkyl group is unsubstituted. Non-limiting examples of ketone solvents include acetone, methylethylketone, and methyl isobutyl ketone (MIBK).

In certain embodiments, the aqueous organic solvent includes a nitrile solvent. The nitrile solvent may be a short chain nitrile having the formula R—CN, wherein R represents a straight or branched C1-C6 alkyl group. In some embodiments, the C1-C6 alkyl group is unsubstituted.

In one embodiment, the aqueous organic solvent is an aqueous acetonitrile. When the aqueous organic solvent is aqueous acetonitrile, the eluent may contain up to 30 wt. % water, between 5 and 25 wt. % water, between 10 and 20 wt. % water, between 15 and 25 wt. % water, and the remainder acetonitrile.

In other embodiments, where the fatty acid ester feedstock comprises a composition that includes components that are more polar and less polar than the polyunsaturated fatty acid esters, the moving ben chromatography unit has a plurality of zones (i.e., having at least a first zone and a second zone), wherein each zone has an extract stream and a raffinate stream from which liquid can be collected from the plurality of linked chromatography columns. In certain embodiments, two or more zones are used (e.g., 2 to 5 zones, 2 or 3 zones, or 2 zones).

In certain embodiments, the components separated in each zone of the plurality of zones have different polarities. In some embodiments, in order to improve on the quality of separation, the raffinate stream collected from one column in the first zone is introduced into a nonadjacent column in the second zone and/or the extract stream from one column in the second zone is introduced into a nonadjacent column in the first zone. In other embodiments, the rate at which liquid collected via the extract and raffinate streams in each zone is recycled back into the same zone is adjusted such that the polyunsaturated fatty acid ester product can be separated from different components of the feed mixture in each zone.

In certain embodiments, the eluting power of the eluent in each of the zones may be different. For example, the eluting power of the eluent in the first zone may be greater than that of the eluent in the second and subsequent zones. In practice, this may be achieved by varying the relative amounts of water:alcohol ratio or water:organic solvent ratio in each zone. Additionally, the recycle rate of the extract and raffinate streams in each zone may be adjusted such that the polyunsaturated fatty acid ester product can be separated from different components of the feed mixture in each zone.

In some embodiments, the water:organic solvent ratio of the eluent in the first zone may be between 5:95 and 25:75 parts by volume, or between 10:90 and 15:85 parts by volume. Alternatively, the water:alcohol or water:organic solvent ratio of the eluent in the first zone may be between 0:100 and 5:95 parts by volume, between 0.1:99.9 and 2.5:97.5 parts by volume, between 0.25:99.75 and 2:98 parts by volume, or between 0.5:99.5 and 1.5:98.5 parts by volume. In these embodiments, the water:alcohol or water:organic solvent ratio of the eluent in the second zone may be between 10:90 and 30:70 parts by volume, or between 15:85 and 20:80 parts by volume. Alternatively, the water:alcohol or water:organic solvent ratio of the eluent in the second zone may be between 3:97 and 7:93 parts by volume, between 4:96 and 6:94 parts by volume, or between 4.5:95.5 and 5.5:94.5 parts by volume. In one embodiment, the water:alcohol or water:organic solvent ratio of the eluent in the first zone is between 0.5:99.5 and 1.5:98.5 parts by volume, and the water:alcohol or water:organic solvent ratio of the eluent in the second zone is between 4.5:95:5 and 5.5:94.5 parts by volume.

Depending on the choice of alcohol or organic solvent, they may be more powerful desorbers than water (e.g., acetonitrile). Alternatively, they may be less powerful desorbers than water. Thus, when the aqueous organic solvent is acetonitrile, for example, the amount of acetonitrile in the eluent in the first zone may be greater than the amount of acetonitrile in the eluent of the second and subsequent zones.

In one particular embodiment, the moving bed separation unit has two zones and the process comprises (i) introducing the fatty acid ester feedstock into the first zone, and removing a first raffinate stream enriched with the polyunsaturated fatty acid esters and a first extract stream depleted of the polyunsaturated fatty acid esters, and (ii) introducing the first raffinate stream into the second zone, removing a second raffinate stream depleted of the polyunsaturated fatty acid esters, and collecting a second extract stream to obtain the polyunsaturated fatty acid esters.

When the apparatus used in the process has two zones, the process comprises introducing the fatty acid ester feedstock to a simulated or actual moving bed chromatography apparatus having a plurality of linked chromatography columns containing, as eluent, an aqueous alcohol or an aqueous organic solvent. The first and second zones each have an extract stream and a raffinate stream from which liquid can be collected from the plurality of linked chromatography columns. In certain embodiments, the raffinate stream containing the polyunsaturated fatty acid esters and any more polar components may be collected from a column in the first zone and introduced to a nonadjacent column in the second zone, and/or an extract stream containing the polyunsaturated fatty acid esters and any less polar components may be collected from a column in the second zone and introduced to a nonadjacent column in the first zone. In such a process, the polyunsaturated fatty acid esters may be separated from less polar components of the fatty acid ester feedstock in the first zone, and the polyunsaturated fatty acid esters may be separated from more polar components of the feed mixture in the second zone.

In certain embodiments, the eluent in the first zone contains more organic solvent than the eluent in the second zone, and the second zone is downstream of the first zone with respect to the flow of eluent in the system. Thus, the eluent in the system may move from the first zone to the second zone. Conversely, the solid adsorbent phase may move from the second zone to the first zone. In certain embodiments, the two zones do not overlap, i.e., there are no chromatographic columns that are in both zones.

In another embodiment, the apparatus has a first zone, a second zone, and a third zone. The water:alcohol ratio or water:organic solvent ratios of the eluent present in the first, second, and third zones may be different. In embodiments when the apparatus has three zones, the eluent in the first zone contains more organic solvent than the eluent in the second and third zones, and the first zone is upstream of the second and third zones with respect to the flow of eluent in the system. Additionally, the eluent in the second zone may contains more organic solvent than the eluent in the third zone and the second zone is upstream of the third zone with respect to the flow of eluent in the system. In certain embodiments, in the first zone, the polyunsaturated fatty acid esters are separated from components of the feed mixture that are less polar than the polyunsaturated fatty acid esters. Additionally, in the second zone, the polyunsaturated fatty acid esters may be separated from components of the feed mixture which are less polar than the polyunsaturated fatty acid esters but more polar than the components separated in the first zone. Further, in the third zone, the polyunsaturated fatty acid esters may be separated from components of the feed mixture which are more polar than the polyunsaturated fatty acid esters. In a further embodiment, in the first zone, the polyunsaturated fatty acid esters are separated from components of the feed mixture which are less polar than the polyunsaturated fatty acid esters; in the second zone, the polyunsaturated fatty acid esters are separated from components of the feed mixture which are more polar than the polyunsaturated fatty acid esters; and in the third zone, the polyunsaturated fatty acid esters are separated from components of the feed mixture which are more polar than the PUFA product and also more polar than the components separated in the second zone.

The operating conditions of the separation process, number of columns in each zone, the dimensions of each zone, the rate of collection, the rate of recycle, the feed rate, and the type of adsorbents may all be varied, based on conventional practice, in order to control the quality of separation of the fatty acid ester feedstock components. Examples of adsorbent materials include polymeric beads, such as polystyrene reticulated with DVB (divinylbenzene); and silica gel, (e.g., reverse phase bonded silica gel with C8 or C18 alkanes). In certain embodiments, the adsorbent is non-polar. The shape of the adsorbent stationary phase material may be, for example, spherical or nonspherical beads. Such beads may have a diameter of 5 to 500 microns, 10 to 500 microns, 15 to 500 microns, 40 to 500 microns, 100 to 500 microns, 250 to 500 microns, 250 to 400 microns, or 250 to 350 microns. In other embodiments, the beads have a diameter of 5 to 35 microns, 10 to 30 microns, or 15 to 25 microns. Use of larger particles may allow for a lower pressure of eluent to be used in the system. In certain embodiments, the adsorbent has a pore size of from 10 to 50 nm, 15 to 45 nm, 20 to 40 nm, or 25 to 35 nm.

For example, the separation process may be conducted at a temperature between 15° C. and 55° C., between 20° C. and 40° C., about 25° C., or about 30° C. Alternatively, the required temperature for the separation process is achieved by heating the chromatographic columns or zones. The heating may be carried out using, for example, an electric heating mantle, a heated water jacket or coil or by radiative heat lamps. The interior and/or exterior of the one or more chromatographic columns are typically heated. The required temperature of at least one of the chromatographic columns may be achieved by heating the columns and/or the aqueous alcohol or aqueous organic solvent eluent, and/or the feed mixture. In certain embodiments, the temperature is greater than 30° C., greater than 35° C., greater than 40° C., greater than 45° C., greater than 50° C., greater than 55° C., or greater than 57° C. The temperature of at least one of the chromatographic columns is up to 100° C., up to 95° C., up to 90° C. up to 85° C., up to 80° C., up to 75° C., or up to 70° C. Thus, temperature ranges for at least one of the chromatographic columns may be from 30 to 100° C., from 35 to 95° C., from 40 to 90° C., from 45 to 85° C., from 50 to 80° C., from 55 to 75° C., or from 57 to 70° C. In other embodiments, the temperature range may be from 40 to 70° C., from 50 to 67° C., from 56 to 65° C., or from 57 to 63° C.

The number of columns used in the apparatus is not particularly limited. In certain embodiments, the number of columns in each zone is 8 or more, or 15 or more, and less than 50 columns, or less than 40. In certain embodiments, each zone includes an approximately equal share of the total number of columns. Thus, in the case of an apparatus configured with two zones, each zone typically consists of approximately half of the total number of chromatographic columns in the system. For example, the first zone may include 4 or more columns, or 8 or more columns. In the same example, the second zone may include 4 or more columns, or 7 or more columns.

In certain embodiments, part of one or more of the extract stream from the first zone, the raffinate stream from the first zone, the extract stream from the second zone, and/or the raffinate stream from the second zone are recycled back into the same zone (e.g., into an adjacent column in the same zone). The recycle may be different from the feeding of an extract or raffinate stream into a nonadjacent column in another zone. For example, the recycle involves feeding part of the extract or raffinate stream out of a zone back into the same zone (e.g., into an adjacent column in the same zone).

Figure 1:
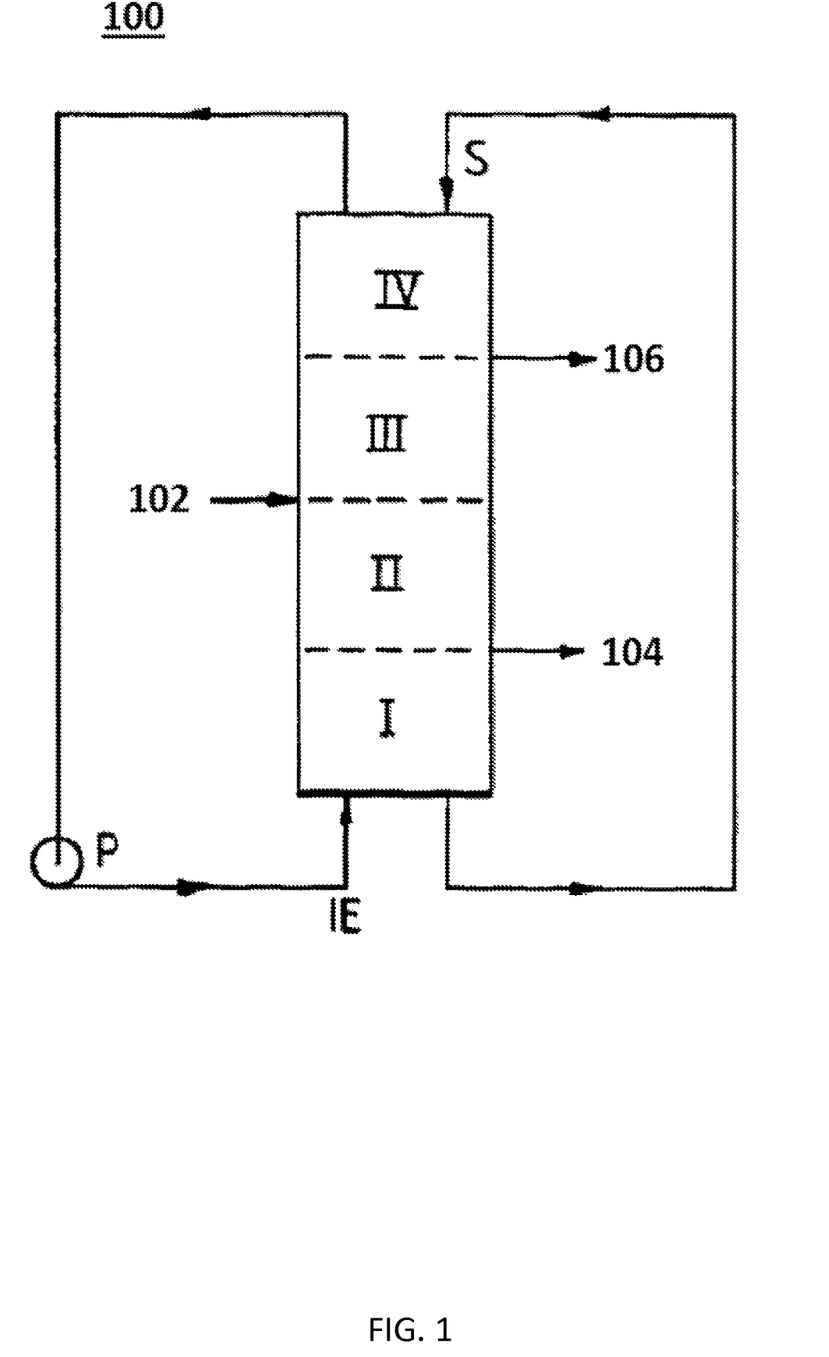
FIG. 1 depicts an embodiment of a method for separating polyunsaturated fatty acid esters and monounsaturated fatty acid esters in a simulating moving bed process.

A non-limiting example of moving bed chromatography apparatus is depicted in FIG. 1. In FIG. 1, a moving bed chromatography unit 100 contains stationary phase S and is divided into four sub-zones I, II, III and IV. The eluent is introduced at the bottom at IE by means of a pump P. The fatty acid ester feedstock having both monounsaturated fatty acid esters and polyunsaturated fatty acid esters is introduced at 102 between sub-zone II and sub-zone III. An extract containing mainly the monounsaturated fatty acid esters is collected at 104 between sub-zone I and sub-zone II, and a raffinate containing mainly the polyunsaturated fatty acid esters is collected at 106 between sub-zone III and sub-zone IV.

Figure 2:
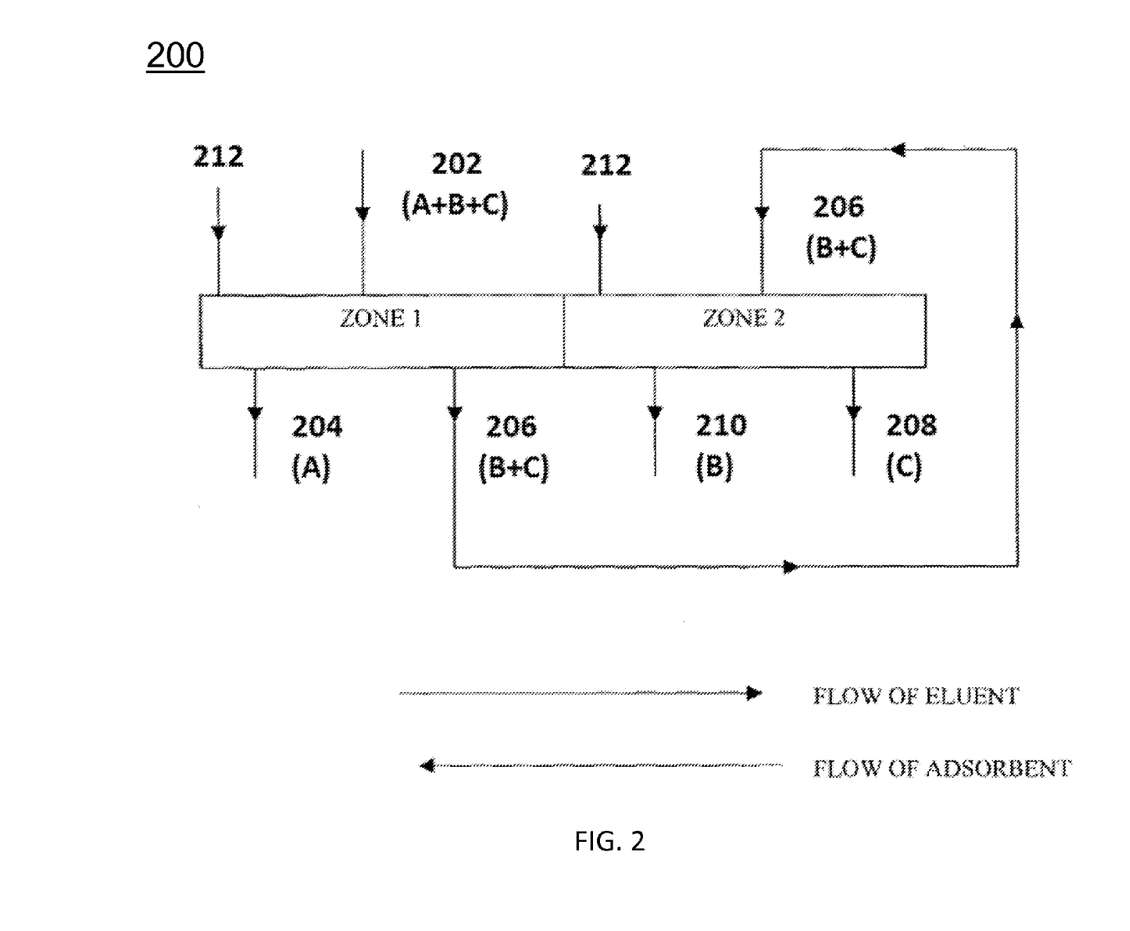
FIG. 2 depicts an embodiment of an additional method for separating polyunsaturated fatty acid esters and monounsaturated fatty acid esters in a simulating moving bed process.

FIG. 2 depicts an additional non-limiting example of moving bed chromatography unit 200 having a plurality of zones (i.e., zones 1 and 2). In this separation unit 200, a fatty acid ester feedstock 202 having polyunsaturated fatty acid esters (B) and more polar (C) and less polar (A) components (e.g., saturated fatty acid esters and monounsaturated fatty acid esters) is introduced into the first zone. An eluent 212 is also introduced into the first and second zones. The eluent may be an aqueous alcohol desorbant, or aqueous organic solvent. In other embodiments, the eluent may be a combination of different streams such as an alcohol desorbant stream and a water stream, or an aqueous organic solvent and a water stream.

In the first zone, the less polar components (A) are removed as extract stream 204. The polyunsaturated fatty acid esters (B) and more polar components (C) are removed as raffinate stream 206. The raffinate stream 206 is then introduced into the second zone. In the second zone, the more polar components (C) are removed as raffinate stream 208. The polyunsaturated fatty acid esters (B) are collected as extract stream 210.

In another alternative embodiment, the monounsaturated fatty acid esters may be designed as stream (B) in FIG. 2, wherein the saturated fatty acid esters represent the less polar components (A) and the polyunsaturated fatty acid esters represent the more polar components (C) in the fatty acid ester feedstock 202. In such an embodiment, the separation unit 200 is designed to separate the monounsaturated fatty acid esters as extract stream 210.

Additional moving bed separation processes and units include those described in U.S. Patent Publication No. 2012/0033043 and International Publication Nos. WO 2013/005046, WO 2013/005047, WO 2013/005048, and WO 2013/005051, herein incorporated by reference in their entireties.

Crystallization Separation

In another embodiment, the separation process is a crystallization separation process. In such a process, prior to any crystallization process, the fatty acid ester feedstock having saturated, monounsaturated, and polyunsaturated fatty acid esters may be sent to a fractional distillation unit to remove any palmitic fatty acid esters or lower (i.e., saturated fatty acid esters having 16 carbon atoms or less). Following the optional fractional distillation, the mixture of saturated, monounsaturated, and polyunsaturated fatty acid esters may be sent to a crystallization unit where the feedstock is cooled down to a temperature lower than at least −37° C. or −60° C. In certain embodiments, a cooling agent is added to the feedstock to assist in the cooling process. The cooling agent may be acetone, or solid carbon dioxide. In other embodiments the feedstock is cooled in a cooling bath, wherein a cooling agent is not necessarily added to the feedstock mixture. After cooling the feedstock, a filtration process may be carried out by suction (at −18° C. in some embodiments), wherein a portion of the feedstock is separated with the filtrate.

Through the crystallization process, it is possible for the polyunsaturated fatty acid esters to be removed from the saturated and monounsaturated fatty acid esters. In one embodiment, the fatty acid ester feedstock is cooled to at least −60° C., wherein polyunsaturated fatty acid esters like linoleic esters are removed through the filtrate. A repetition of crystallizations may be required to adequately separate the various components of the fatty acid ester feedstock (e.g., to separate at least 50 wt. %, at least 60 wt. %, at least 70 wt. %, at least 80 wt. %, at least 90 wt. %, at least 95 wt. %, or at least 99 wt. % of the polyunsaturated fatty acid esters from the remaining fatty acid ester compounds).

If desired, following separation of the polyunsaturated fatty acid esters from the saturated and monounsaturated fatty acid esters, an additional crystallization process may be provided to separate the saturated fatty acid esters from the monounsaturated fatty acid esters.

Formation/Source of Polyunsaturated and Monounsaturated Fatty Acid Esters

In certain embodiments, the fatty acid ester feedstock having monounsaturated fatty acid esters, polyunsaturated fatty acid esters, and (optionally) saturated fatty acid esters is derived from a natural oil feedstock. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil.

In certain embodiments, the natural oil may be treated to render the natural oil more suitable for a downstream metathesis reaction. In one embodiment, the treatment of the natural oil involves the removal of catalyst poisons, such as peroxides, which may potentially diminish the activity of the metathesis catalyst. Non-limiting examples of natural oil feedstock treatment methods to diminish catalyst poisons include those described in PCT/US2008/09604, PCT/US2008/09635, and U.S. Patent Application Publication Nos. 2011/0160472 and 2011/0313180, herein incorporated by reference in their entireties.

After the optional treatment of the natural oil feedstock, the natural oil may be sent to a transesterification unit. Within the transesterification unit, the natural oil may be reacted with at least one alcohol in the presence of a transesterification catalyst. In certain embodiments, the alcohol comprises a monohydric alcohol. In some embodiments, the monohydric alcohol is methanol and/or ethanol. In another embodiment, the alcohol comprises glycerol (and the transesterification reaction is a glycerolysis reaction). In one embodiment, the transesterification reaction is conducted at approximately 60-70° C. and approximately 1 atm. In certain embodiments, the transesterification catalyst is a homogeneous sodium methoxide catalyst. Varying amounts of catalyst may be used in the reaction, and, in certain embodiments, the transesterification catalyst is present in the amount of approximately 0.5-1.0 weight % of the natural oil.

In certain embodiments, the transesterification reaction may produce a transesterified product that may be used as a component of the fatty acid ester feedstock. The transesterified product may comprise saturated and/or unsaturated fatty acid monoesters (e.g., fatty acid methyl esters or "FAME"), glycerin, methanol, and/or free fatty acids. In certain embodiments, the transesterified product comprises monounsaturated fatty acid esters and polyunsaturated fatty acid esters. In some embodiments, the location of the unsaturation for the monounsaturated fatty acid esters is between the C9-C10 positions, as measured from the ester moiety.

In certain embodiments, the transesterified products from the transesterification unit 20 can be sent to a liquid-liquid separation unit, wherein the transesterified products (e.g., FAME, free fatty acids, and/or alcohols) are separated from glycerin. Additionally, in certain embodiments, the glycerin byproduct stream may be further processed in a secondary separation unit, wherein the glycerin is removed and any remaining alcohols are recycled back to the transesterification unit for further processing.

In certain embodiments, the transesterified products can be sent to a hydrogenation unit for selective hydrogenation, wherein the concentration of monounsaturated fatty acid esters is increased by selectively hydrogenating the polyunsaturated fatty acid esters. Non-limiting examples of dieneselective hydrogenation mechanisms are described in U.S. Patent Publication No. 2013/0217906, herein incorporated by reference in its entirety. In certain embodiments, in the selective hydrogenation, the conversion rate from the transesterified polyunsaturated fatty acid esters to saturated and monounsaturated transesterified fatty acid esters may be at least 50%, at least 75%, at least 85%, at least 95%, or at least 98%. The selectivity towards the monounsaturated fatty acid esters instead of saturated fatty acid esters is at least 90%, at least 95%, at least 99%, or at least 99.5%.

In one embodiment, the transesterified products or selectively hydrogenated transesterified products are further processed in a water-washing unit. In this unit, the transesterified products undergo a liquid-liquid extraction when washed with water. Excess alcohol, water, and glycerin are removed from the transesterified products. In another embodiment, the water-washing step is followed by a drying unit in which excess water is further removed.

In certain embodiments, prior to a separation of polyunsaturated compounds from monounsaturated compounds, the fatty acid ester compounds in the transesterified product may undergo a hydrolysis reaction with water to provide a hydrolyzed product comprising acid compounds. Following hydrolysis, in some embodiments, the hydrolyzed product may be sent to a flash column or decanter to remove methanol and water from the acids.

Metathesis of Monounsaturated Fatty Acid Esters and Processing of Metathesized Feedstock Following separation of the polyunsaturated fatty acid esters from the monounsaturated fatty acid esters (and, optionally, the saturated fatty acid esters), the monounsaturated fatty acid esters (and, optionally, saturated fatty acid esters) may be sent to a metathesis reaction unit. In the metathesis reaction unit, the monounsaturated fatty acid esters may be self-metathesized or cross-metathesized with an olefin feedstock in the presence of a metathesis catalyst, thereby providing a metathesized feedstock.

Based on the upstream separation process to remove a majority of the polyunsaturated fatty acid esters from the monounsaturated fatty acid ester composition, this downstream metathesis process may allow for the formation of a highly tailored metathesized feedstock. For example, in certain embodiments, a majority of the monounsaturated fatty acid esters have a single unsaturated carbon-carbon double bond located at the same position on the carbon chain as measured from the acid or ester. Additionally, the majority of monounsaturated fatty acid esters have the same overall carbon chain length. Therefore, with the removal of the polyunsaturated fatty acid esters, these downstream cross-metathesis reactions may occur primarily at the same position, allowing for a targeted metathesized ester product as well at least one olefin, based on the selected olefin feedstock. In certain embodiments, at least 50 wt. %, 60 wt. %, 70 wt. %, 80 wt. %, 90 wt. %, or 95 wt. % of the monounsaturated fatty acid esters have the same carbon chain length and the location of the unsaturated carbon-carbon double bonds at the same position. For example, in one embodiment, a majority of monounsaturated fatty acid esters have a carbon chain length of 18 carbon atoms and a single unsaturated carbon-carbon double bond between the C9 and C10 position on the carbon chain, as measured from the acid or ester.

The metathesis catalyst includes any catalyst or catalyst system that catalyzes a metathesis reaction. Any known or future-developed metathesis catalyst may be used, individually or in combination with one or more additional catalysts. Non-limiting exemplary metathesis catalysts and process conditions are described in PCT/US2008/009635, incorporated by reference herein. A number of the non-limiting metathesis catalysts are commercially available from Materia, Inc. (Pasadena, Calif.) and XiMo, Inc. (Budapest, Hungary). The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent may be an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, in the presence of the metathesis catalyst, the monounsaturated fatty acid esters undergo a cross-metathesis reaction with the olefin feedstock.

Additionally, in certain embodiments, the olefin feedstock may also be treated, in combination with or separately from the natural oil feedstock, prior to the metathesis reaction. Like the natural oil treatment, the olefin feedstock may be treated to remove poisons that may impact or diminish catalyst activity using any of the above-mentioned methods of treatment.

In other embodiments, the olefin feedstock is isomerized prior to being metathesized with the natural oil. Adjusting the composition and properties of the olefin feedstock through isomerization may allow for different products or different ratios of products to be formed following metathesis of the olefin feedstock (e.g., low-weight olefin, mid-weight olefin, and/or high-weight olefin) with a natural oil. By using branched low-weight olefins, branched mid-weight olefins, or branched high-weight olefins in the metathesis reaction, the metathesized product will include branched olefins, which can be subsequently hydrogenated to iso-paraffin.

In certain embodiments, the olefin feedstock comprises low-weight olefins in the C2 to C6 range or the C4 to C10 range. In another embodiment, the olefin feedstock comprises at least one alpha-olefin in the C2 to C10 range or the C4 to C10 range. In another embodiment, the olefin feedstock comprises at least one branched low-weight olefin in the C4 to C10 range.

In certain embodiments, the olefin feedstock comprises mid-weight olefins having unsaturated straight, branched, or cyclic hydrocarbons in the C15 to C24 range. In some embodiments, the mid-weight olefin is an alpha-olefin. In some embodiments, the mid-weight olefin is an alpha-olefin selected from the group consisting of 1-pentadecene, 1-hexadecene, 1-heptadecene, 1-octadecene, 1-nonadecene, 1-icosene, 1-henicosene, 1-tricosene, 1-tetracosene, and combinations thereof. In one particular embodiment, the mid-weight olefin is 1-octadecene. In other embodiments, the mid-weight olefin comprises a mixture of C15-C24 alpha olefins, C17-C21 alpha olefins, C18-C24 alpha olefins, or C20-C24 alpha olefins.

In certain embodiments, the olefin feedstock comprises high-weight olefins having unsaturated straight, branched, or cyclic hydrocarbons in the C25+, C25-C100, or C25-C36 range. In some embodiments, the high-weight olefin is an alpha-olefin.

As noted, it is possible to use a mixture of various linear or branched olefins in the reaction to achieve the desired metathesis product distribution. In certain embodiments, the mixture comprises linear and/or branched low-weight olefins. In other embodiments, the mixture comprises linear and/or branched mid-weight olefins. In other embodiments, the mixture comprises linear and/or branched high-weight olefins. In one embodiment, a mixture of butenes (1-butene, 2-butenes, and, optionally, isobutene) may be employed as the low-weight olefin, offering a low cost, commercially available feedstock instead a purified source of one particular butene. Such low cost mixed butene feedstocks may be diluted with n-butane and/or isobutane.

In another embodiment, the olefin feedstock is a symmetric internal olefin having the structure $R^1CH=CHR^2$, wherein $R^1$ and $R^2$ represent the same organic group. The organic group may be an aliphatic group, an alicyclic group, or an aromatic group. Organic groups may optionally include heteroatoms (e.g., O, N, or S atoms), as well as functional groups (e.g., carbonyl groups). The term aliphatic group means a saturated or unsaturated, linear or branched, hydrocarbon group. This term is used to encompass alkyl groups. The term alkyl group means a monovalent, saturated, linear, branched, or cyclic hydrocarbon group. Representative examples of alkyl groups include methyl, ethyl, propyl (n-propyl or i-propyl), butyl (n-butyl or t-butyl), pentyl, hexyl, and heptyl. An alicyclic group is an aliphatic group arranged in one or more closed ring structures. The term is used to encompass saturated (i.e., cycloparaffin) or unsaturated (cycloolefins or cycloacetylenes) groups. An aromatic or aryl group is an unsaturated cyclic hydrocarbon having a conjugated ring structure. Included within aromatic or aryl groups are those possessing both an aromatic ring structure and an aliphatic or alicyclic group. In certain embodiments, the symmetric internal olefin is 2-butene or 3-hexene. In such a reaction mechanism with a symmetric internal olefin such as 3-hexene, the cross-metathesis product may primarily include a single internal-olefin ester (e.g., 9-dodecenoic ester) along with internal olefin compositions (e.g., 3-dodecene).

In one particular embodiment, the olefin feedstock is ethylene. When ethylene is cross-metathesized with the monounsaturated fatty acid esters (e.g., fatty acid esters having a carbon-carbon double bond between the C9 and C10 positions), the cross-metathesis product may include a single terminal-olefin fatty acid ester (e.g., 9-decenoic acid methyl ester, 9-DAME) along with terminal olefin compositions (e.g., 1-decene). Through such a reaction mechanism, an improved, higher purity or valuable product may be targeted with minimal or no downstream separation steps to remove various ester compositions from each other. In certain embodiments, the metathesized ester in the metathesized product is at least 50 wt. % 9-decenoic ester (i.e., more than 50 wt. % of the metathesized fatty acid esters in the metathesized product are 9-decenoic acid or 9-decenoic acid ester). In other embodiments, more than 60 wt. %, more than 70 wt. %, more than 80 wt. %, more than 90 wt. %, or more than 95 wt. % of the metathesized fatty acid esters in the metathesized product is 9-decenoic acid, 9-decenoic acid ester, or combinations thereof.

In one particular embodiment, the olefin feedstock is 1-butene. When 1-butene is cross-metathesized with the monounsaturated fatty acid esters (e.g., fatty acid esters having a carbon-carbon double bond between the C9 and C10 positions), the cross-metathesis product will include a combination of fatty acid esters having terminal carbon-carbon double bond compositions and internal carbon-carbon double bond compositions, along with terminal olefins and internal olefins. For example, the following are produced when 9 methyl oleate (9-octadecenoate methyl ester) is cross-metathesized with 1-butene: 9-decenoic acid methyl ester (9-DAME), 9-dodecenoic acid methyl ester (9-DDAME), 1-decene, and 3-dodecene.

In one aspect of the invention, wherein two different esters are produced by cross-metathesis of an asymmetric olefin, such as 1-butene; there is provided the option of recycling the less desired ester to the metathesis step. In this way, the output of the more desired metathesized fatty acid ester is increased. For example, this option may be used for the case where 9-DAME and 9-DDAME are produced from the cross-metathesis of methyl oleate with 1-butene. If the 9-DAME is more valuable, it is preferred to separate the 9-DAME and 9-DDAME and feed at least a portion of the 9-DDAME back to the metathesis step. The 1-butene will cross-metathesize a portion of the recycled 9-DDAME and provide additional 9-DAME. The cross-metathesis conditions and the degree of separation and recycling can be tuned so as to drive higher yield of the 9-DAME (e.g., approach 100%) from the process. Alternatively, if the 9-DDAME is the metathesized fatty acid ester with a higher value, it is likewise possible to recycle the 9-DAME to drive higher output of the 9-DDAME.

An advantage of implementing the recycling option to increase output of a more desired metathesized fatty acid ester is that it can be greatly enhance the flexibility of the biorefinery. In other words, if the value of the two metathesized fatty acid esters produced is relatively equal, there is no need to engage the recycling option. However, if either one of the two metathesized fatty acid esters is more valuable, the recycling option can be engaged to increase the output of whichever metathesized fatty acid ester has more value.

In certain embodiments, the metathesized feedstock comprises metathesized fatty acid esters and at least one metathesized olefin. In some embodiments, the metathesized feedstock may be sent to a separation unit to separate the metathesized fatty acid esters and the at least one metathesized olefin.

In certain embodiments, prior to or following the separation unit, the metathesized fatty acid esters may undergo a hydrolysis reaction with water to provide a hydrolyzed product comprising acid compounds. Following hydrolysis, in some embodiments, the hydrolyzed product may be sent to a flash column or decanter to remove methanol and water from the acids.

Processing of Polyunsaturated Fatty Acid Esters

Following separation of the polyunsaturated fatty acid esters from the monounsaturated fatty acid esters (and, optionally, saturated fatty acid esters), the polyunsaturated fatty acid esters are further processed.

In one embodiment, the polyunsaturated fatty acid esters are combined with hydrogen in a hydrogenation unit to selectively or fully hydrogenate the polyunsaturated fatty acid esters and provide an at least partially hydrogenated fatty acid ester product. Non-limiting examples of diene-selective hydrogenation mechanisms are described in U.S. Patent Publication No. 2013/0217906, herein incorporated by reference in its entirety. In some embodiments, the reaction forms a mixture of saturated fatty acid esters, monounsaturated fatty acid esters, and unreacted polyunsaturated fatty acid esters. In one embodiment, the polyunsaturated fatty acid esters are selectively hydrogenated, wherein the polyunsaturated fatty acid esters are converted into saturated and monounsaturated fatty acid esters. In certain embodiments, the conversion rate from the transesterified polyunsaturated fatty acid esters to saturated and monounsaturated transesterified fatty acid esters may be at least 50%, at least 75%, at least 85%, at least 95%, or at least 98%. In some embodiments, the selectivity towards the monounsaturated fatty acid esters instead of saturated fatty acid esters is at least 90%, at least 95%, at least 99%, or at least 99.5%.

In another embodiment, the polyunsaturated fatty acid esters are "fully" hydrogenated, wherein more than 95% of the polyunsaturated fatty acid esters are converted into saturated fatty acid esters.

Following the hydrogenation unit, the at least partially hydrogenated fatty acid esters may be further processed downstream or sent to an external facility for use as a biodiesel. In another embodiment, the at least partially hydrogenated fatty acid esters may be sent to a separation unit for further processing/separation. A portion of the at least partially hydrogenated fatty acid esters containing monounsaturated fatty acid esters may be recycled back to the separation unit in order to capture additional monounsaturated fatty acid esters that could be sent to the metathesis reaction unit. Another portion of at least partially hydrogenated fatty acid esters containing saturated fatty acid esters may be further processed downstream or sent to an external facility for use as a biodiesel.

In certain embodiments, prior to the separation of the polyunsaturated compounds from the monounsaturated compounds (and, optionally, saturated compounds), the fatty acid ester compounds may be subjected to a hydrolysis reaction with water to provide a hydrolyzed product comprising acid compounds. Following hydrolysis, in some embodiments, the hydrolyzed product may be sent to a flash column or decanter to remove methanol and water from the acids.

Biorefinery

In certain embodiments, a selected group of the reaction mechanisms and separation processes discussed above may be implemented in a biorefinery design unit, wherein a natural oil feedstock is converted to make specialty chemicals, such as high value esters and olefins, and fuels, such as biodiesel, etc.

Figure 3:
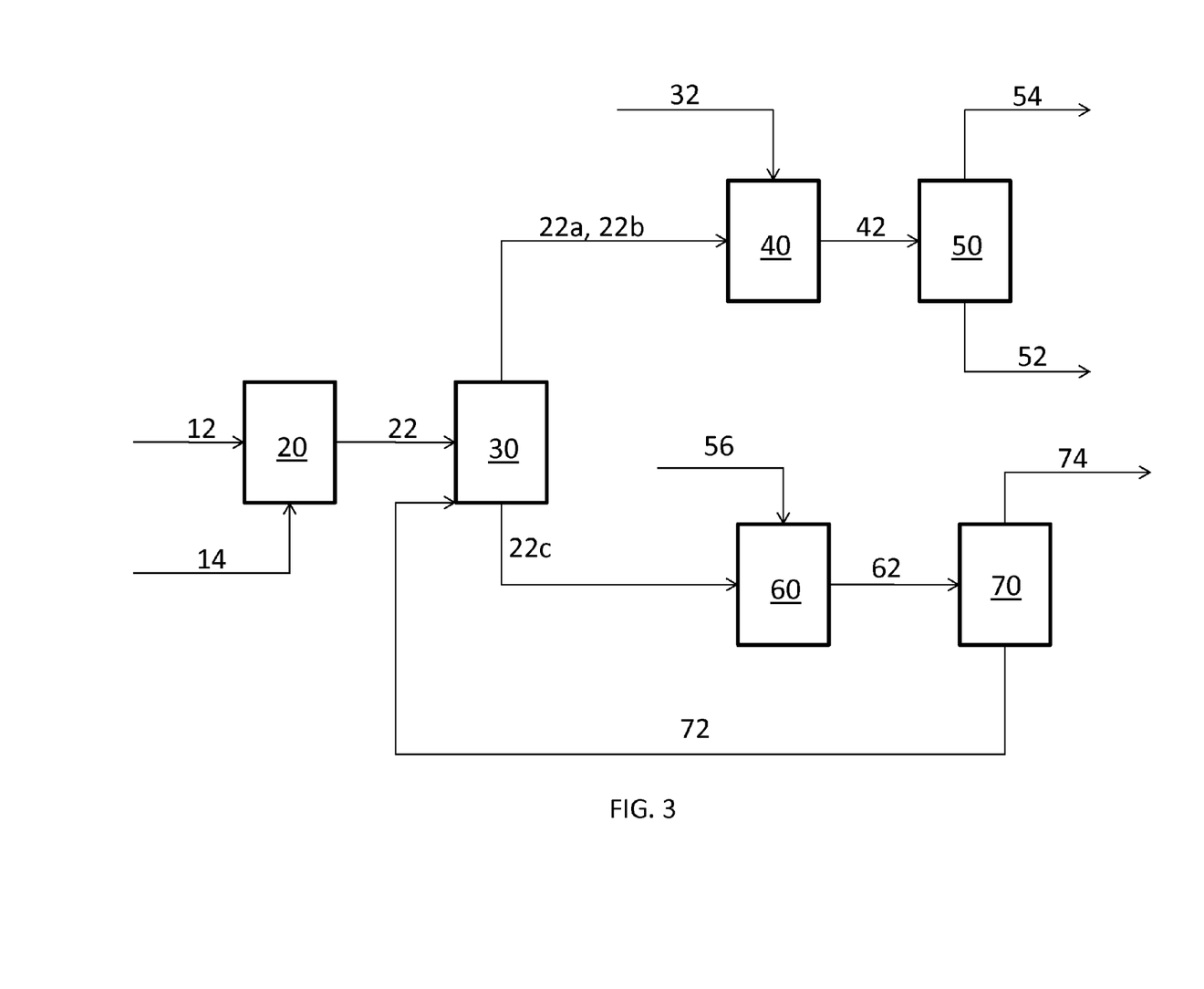
FIG. 3 depicts a schematic diagram of one embodiment of a process of converting a natural oil feedstock into polyunsaturated fatty acid esters and monounsaturated fatty acid esters.

One embodiment of a biorefinery design is represented in FIG. 3. As shown in FIG. 3, a natural oil feedstock 12 is sent to a transesterification unit 20. Within the transesterification unit 20, the natural oil 12 is reacted with at least one alcohol 14 in the presence of a transesterification catalyst. The transesterification reaction may produce a transesterified product that may be used as a component of a fatty acid ester feedstock 22 having monounsaturated fatty acid esters, polyunsaturated fatty acid esters, and (optionally) saturated fatty acid esters.

The fatty acid ester feedstock 22 is sent to a separation unit 30. In certain embodiments, the fatty acid ester feedstock comprises a mixture of saturated fatty acid esters 22a, monounsaturated fatty acid esters 22b, and polyunsaturated fatty acid esters 22c.

In certain embodiments, the polyunsaturated fatty acid esters 22c are separated from the saturated fatty acid esters 22a and the monounsaturated fatty acid esters 22b. In certain embodiments, the separation unit 30 is an actual or simulated moving bed chromatographic separation unit, a crystallization separation unit, a membrane separation unit, a distillation separation unit, or combination thereof.

As shown in FIG. 3, following separation of the polyunsaturated fatty acid esters 22c from the saturated fatty acid esters 22a and monounsaturated fatty acid esters 22b, the saturated and monounsaturated fatty acid esters are sent to a metathesis reaction unit 40. In the metathesis reaction unit, the monounsaturated fatty acid esters 22b may be self-metathesized or cross-metathesized with an olefin feedstock 32 in the presence of a metathesis catalyst, thereby forming a metathesized feedstock 42. In certain embodiments, in the presence of the metathesis catalyst, the monounsaturated fatty acid esters 22b undergo a cross-metathesis reaction with the olefin feedstock 32.

In certain embodiments, the metathesized feedstock 42 comprises metathesized fatty acid esters 52 and at least one metathesized olefin 54. In some embodiments, the metathesized feedstock 42 may be sent to a separation unit 50 to separate the metathesized fatty acid esters 52 from the at least one metathesized olefin 54, or to separate certain metathesized fatty acid esters from other metathesized fatty acid esters. In some embodiments, at least a portion of the metathesized fatty acid esters are recycled back to the metathesis reaction unit.

As shown in FIG. 3, following separation of the polyunsaturated fatty acid esters 22c from the saturated fatty acid esters 22a and monounsaturated fatty acid esters 22b, the polyunsaturated fatty acid esters 22c may be further processed.

In one embodiment, the polyunsaturated fatty acid esters 22c are combined with hydrogen 56 in a hydrogenation unit 60 to selectively or fully hydrogenate the polyunsaturated fatty acid esters and provide an at least partially hydrogenated acid ester product 62.

Following the hydrogenation unit 60, the at least partially hydrogenated acid esters 62 may be further processed downstream or sent to an external facility for use as a biodiesel. In another embodiment, the at least partially hydrogenated acid esters 62 may be sent to a separation unit 70 for further processing/separation. A portion of the at least partially hydrogenated acid esters 72 containing monounsaturated fatty acid esters may be recycled back to the separation unit 30 in order to capture additional monounsaturated fatty acid esters that could be sent to the metathesis reaction unit 40. Another portion of at least partially hydrogenated acid esters 74 containing saturated fatty acid esters may be further processed downstream or sent to an external facility for use as a biodiesel.

Figure 4:
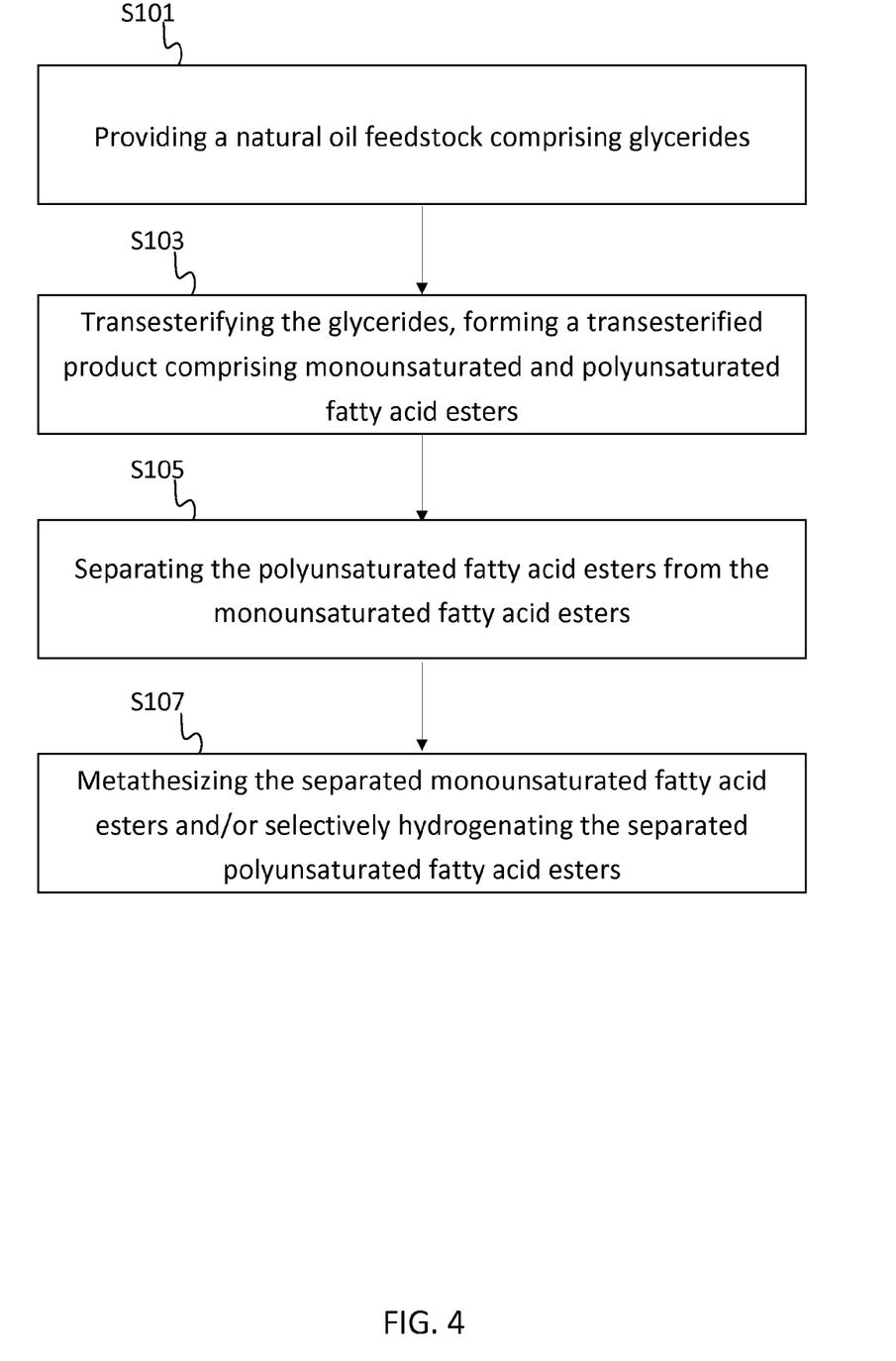
FIG. 4 depicts an example flowchart for converting a natural oil feedstock into polyunsaturated fatty acid esters and monounsaturated fatty acid esters.

FIG. 4 illustrates an example flowchart for refining natural oil feedstocks and derivatives thereof. In act S101, a natural oil feedstock comprising glycerides is provided. Natural oil glycerides may comprise monoglycerides, diglycerides, triglycerides, or mixtures thereof, including various natural oil feedstocks and natural oil derivatives defined below. In act S103, the glycerides are transesterified with a monohydric alcohol or alkanol to provide a transesterified product comprising monounsaturated fatty acid esters and polyunsaturated fatty acid esters. In act S105, the polyunsaturated fatty acid esters are separated from the monounsaturated fatty acid esters, forming separated polyunsaturated fatty acid esters and separated monounsaturated fatty acid esters. In act S107, (1) the separated monounsaturated fatty acid esters are metathesized in the presence of a metathesis catalyst to provide a metathesized product comprising metathesized monounsaturated fatty acid esters and at least one olefin, and/or (2) the separated polyunsaturated fatty acid esters are selectively hydrogenated and recycled to the separation unit.

DEFINITIONS

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In other embodiments, the natural oil derivative is a monoglyceride or diglyceride composition. In some embodiments, a feedstock includes canola or soybean oil, as a non-limiting example, refined, bleached, and deodorized soybean oil (i.e., RBD soybean oil). Soybean oil may comprise about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, "natural oil glycerides" or "glycerides" refer to compositions comprising monoglycerides, diglycerides, triglycerides, or mixtures thereof, including various natural oil feedstocks and natural oil derivatives discussed above.

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to provide a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis)

in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, the terms "olefin," "olefins," and "olefin feedstock" may refer to hydrocarbon compounds having at least one unsaturated carbon-carbon double bond. In certain embodiments, the terms "olefin," "olefins," and "olefin feedstock" may refer to a group of unsaturated carbon-carbon double bond compounds with different carbon lengths, such as "low-weight olefins," "mid-weight olefins," "high-weight olefins," or mixtures thereof. Unless noted otherwise, the term "olefin," "olefins," and "olefin feedstock" encompasses "polyunsaturated olefins" or "poly-olefins" having more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin," while an olefin having a non-terminal carbon-carbon double bond can be referred to as an "internal olefin." It is also noted that the olefin feedstock may be sourced or purchased from a third-party, external source. In other embodiments, the olefin feedstock may be derived from a natural oil, as described in further detail below. In yet other embodiments, the olefin feedstock may be synthesized from bacteria (e.g., through fatty acid decarboxylase from *Jeotgalicoccus* species, as described in Rude et al., "Terminal Olefin (1-Alkene) Biosynthesis by a Novel P450 Fatty Acid Decarboxylase from *Jeotgalicoccus* Species," *Applied and Environmental Microbiology*, March 2011, pp. 1718-1727).

As used herein, the term "low-weight olefin" may refer to any one or combination of unsaturated straight, branched, or cyclic hydrocarbons in the C2 to C14 range. Low-weight olefins include "alpha-olefins" or "terminal olefins," wherein the unsaturated carbon-carbon bond is present at one end of the compound. Low-weight olefins may also include polyunsaturated olefins (e.g., dienes and trienes). Low-weight olefins may also include internal olefins or "low-weight internal olefins." In certain embodiments, the low-weight internal olefin is in the C4 to C14 range. Examples of low-weight olefins in the C2 to C6 range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-weight olefins in the C7 to C9 range include 1,4-heptadiene, 1-heptene, 3,6-nonadiene, 3-nonene, 1,4,7-octatriene. Other possible low-weight olefins include styrene, vinyl cyclohexane, cardanol, limonene, and isoprene. In certain embodiments, a mixture of olefins may be provided, wherein the mixture may include linear and/or branched low-weight olefins in the C4-C10 range. In one embodiment, the mixture includes linear and branched C4 olefins (i.e., combinations of: 1-butene, 2-butene, and/or isobutene). In other embodiments, a higher range of C11-C14 may be used.

As used herein, the term "mid-weight olefin" may refer to any one or combination of unsaturated straight, branched, or cyclic hydrocarbons in the C15 to C24 range. Mid-weight olefins include "alpha-olefins" or "terminal olefins," wherein the unsaturated carbon-carbon bond is present at one end of the compound. Mid-weight olefins may also include polyunsaturated olefins (e.g., dienes and trienes). Mid-weight olefins may also include internal olefins or "mid-weight internal olefins." In certain embodiments, a mixture of olefins may be provided. In certain embodiments, the mid-weight olefin comprises C15-C24 alpha olefins, C17-C21 alpha olefins, C18-C24 alpha olefins, or C20-C24 alpha olefins.

As used herein, the term "high-weight olefin" may refer to any one or combination of unsaturated straight, branched, or cyclic hydrocarbons comprising 25+ carbon atoms, or unsaturated hydrocarbons in the C25-C100 or C25-C36 range. High-weight olefins include "alpha-olefins" or "terminal olefins," wherein the unsaturated carbon-carbon bond is present at one end of the compound. High-weight olefins may also include polyunsaturated olefins (e.g., dienes and trienes). High-weight olefins may also include internal olefins or "high-weight internal olefins." In certain embodiments, a mixture of olefins may be provided. In certain embodiments, the high-weight olefin comprises C25+ alpha olefins, C25-C100 alpha olefins, or C25-C36 alpha olefins.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "alpha-olefin" refers to an olefin (as defined above) that has a terminal carbon-carbon double bond. In some embodiments, the alpha-olefin is a terminal alkene, which is an alkene (as defined above) having a terminal carbon-carbon double bond. Additional carbon-carbon double bonds can be present.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified. Thus, the term "unsaturated glyceride" can refer to monoglycerides, diglycerides, or triglycerides, where one or more of the acid portions of the ester contain unsaturation, e.g., a carbon-carbon double bond.

It is noted that an olefin may also comprise an ester, and an ester may also comprise an olefin, if the R or R' group in the general formula R—COO—R' contains an unsaturated carbon-carbon double bond. Such compounds can be referred to as "olefin esters." Further, a "terminal olefin ester" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "acid" or "acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "acids" may refer to a group of compounds with the general formula described above, wherein the compounds have different carbon lengths. The term "carboxyl" refers to a —COOH moiety. The term "carboxylated" refers to a "carboxyl" group formed on another group or compound.

As used herein, "alcohol" or "alcohols" refer to compounds having the general formula: R—OH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. The term "hydroxyl" refers to a —OH moiety. In certain embodiments, the alcohol is a monohydric alcohol or "alkanol."

As used herein, the term "alkanol" may refer to aliphatic alcohols with the general formula $C_nH_{2n+2}O_1$. In certain embodiments, the alkanol is a primary or secondary alcohol, such as one or more of methanol, ethanol, n-propanol, isopropanol, n-butanol, 2-butanol, isobutanol, n-pentanol, or n-hexanol.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which are groups of the following formulas: -[-(alkylene)-O—]$_x$-alkyl, or -[-(alkylene)-O—]$_x$-alkylene-, respectively, where x is 1 or more, such as 1, 2, 3, 4, 5, 6, 7, or 8.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "C2-6 alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group, respectively.

As used herein, "alkynyl" refers to a straight or branched chain non-aromatic hydrocarbon having 2 to 30 carbon atoms and having one or more carbon-carbon triple bonds, which may be optionally substituted, as herein further described, with multiple degrees of substitution being allowed. Examples of "alkynyl," as used herein, include, but are not limited to, ethynyl, 2-propynyl, 2-butynyl, and 3-butynyl. The number of carbon atoms in an alkynyl group is represented by the phrase "$C_{x-y}$ alkynyl," which refers to an alkynyl group, as herein defined, containing from x to y, inclusive, carbon atoms. Thus, "Cm alkynyl" represents an alkynyl chain having from 2 to 6 carbon atoms and, for example, includes, but is not limited to, ethynyl, 2-propynyl, 2-butynyl, and 3-butynyl. In some instances, the "alkynyl" group can be divalent, in which case the group can alternatively be referred to as an "alkynylene" group. Also, in some instances, one or more of the saturated carbon atoms in the alkynyl group can be replaced by a heteroatom (e.g., selected from nitrogen, oxygen, or sulfur, including N-oxides, sulfur oxides, and sulfur dioxides, where feasible), and is referred to as a "heteroalkynyl" group.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . ." or "substituted one or more times . . ." refer to a number of substituents that equals from one to the maximum number of substituents possible based on the number of available bonding sites, provided that the above conditions of stability and chemical feasibility are met.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "zone" may refer to a plurality of linked chromatography columns containing, as eluent, an aqueous alcohol or aqueous organic solvent, and having one or more injection points for a feed mixture stream, one or more injection points for water, alcohol, and/or organic solvent, a raffinate take-off stream from which liquid can be collected from said plurality of linked chromatography columns, and an extract take-off stream from which liquid can be collected from said plurality of linked chromatography columns. Each zone may have only one injection point for a feed mixture. In one embodiment, each zone has only one injection point for the aqueous alcohol or aqueous organic solvent eluent. In another embodiment, each zone has two or more injection points for water, alcohol, and/or organic solvent.

The term "raffinate" may refer to the stream of components that move more rapidly with the liquid eluent phase compared with the solid adsorbent phase. Thus, a raffinate stream may be enriched with more polar components, and depleted of less polar components compared with a feed stream.

The term "extract" may refer to the stream of components that move more rapidly with the solid adsorbent phase compared with the liquid eluent phase. Thus, an extract stream may be enriched with less polar components, and depleted of more polar components compared with a feed stream.

As used herein the term "nonadjacent" when applied to columns in the same apparatus refers to columns separated by one or more columns, 3 or more columns, 5 or more columns, or about 5 columns.

Other terms are defined in other portions of this description, even though not included in this subsection.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

EXAMPLES

Example 1

Generation of Fatty Acid Ester Stream

Fatty acid methyl esters (FAMEs) were derived from palm oil, which contained FAMEs in the following amounts (wt %): C16:0, 48%; C18:0, 4.5%; C18:1, 37.7%; C18:2, 8%; and C18:3, 0.1%. (Note that the nomenclature CXX:Y refers to a fatty acid methyl ester, where the fatty acid contains XX number of carbon atoms and Y number of carbon-carbon double bonds.) The FAMEs were prepared by transesterification of palm oil with methanol, according to standard methods known in the art.

In a metathesis-based biorefinery (described above) the saturated FAMEs are effectively inert, as they have no carbon-carbon double bonds. Therefore, the FAME stream described above was distilled to remove some portion of methyl palmitate (C16:0 methyl ester). This concentrated the stream in C18 FAMEs (both saturated and unsaturated). The concentrated FAME stream was used for the separation experiments described below.

Example 2

Separation of Monounsaturated Fatty Acid Esters

The post-distillation sample from Example 1 was treated using a simulated moving bed (SMB) chromatography. In this example, the SMB unit is set to operate on the principle of preferential adsorption of saturated and monounsaturated fatty acid methyl esters relative to polyunsaturated fatty acid methyl esters. The ORPHEUS adsorbent (Orochem Technologies Inc., Naperville, Ill., USA) was used as the adsorbent. Methanol was used as the desorbing solvent. The saturated methyl esters and C18:1 unsaturated methyl esters were preferentially adsorbed in a first zone of the adsorbent bed. In a second zone, the C18:2 methyl esters and the C18:3 methyl esters were removed from the pores of the adsorbent by the methanol desorbent. In a third zone of the bed, the saturated methyl esters and C18:1 unsaturated methyl esters were desorbed from the adsorbent by methanol. The mixture of the rejected portion of the feed (raffinate) and methanol was then sent to a distillation column to recover and recycle the methanol desorbent and produce the raffinate stream containing primarily the C18:2 unsaturated methyl esters and the C18:3 unsaturated methyl esters. The extract stream including a mixture of saturated methyl esters and C18:1 unsaturated methyl esters and methanol was sent to a distillation column. In this column, methanol was recovered and recycled to the process. The extract product contained primarily the saturated methyl esters and C18:1 unsaturated methyl esters and other monounsaturated methyl esters in the feed. Table 1, below, shows the results of the separation. The C18:1 unsaturated methyl ester recovery was 93.7%, based on the amount contained in the feed. The saturated methyl esters and C18:1 unsaturated methyl ester purity in the SMB product was 99.7 wt %.

TABLE 1

| Composition (wt %) | Feed | SMB Product | SMB Reject |
| --- | --- | --- | --- |
| C16:0 ME | 3.4 | 2.5 | 6.2 |
| C18:0 ME | 8.3 | 10.4 | 1.3 |
| C20:0 ME | 0.8 | 0.8 | 0.7 |
| C16:1 ME | 0.1 | 0.2 | 0 |
| C18:1 ME | 69.1 | 85.2 | 18 |
| C20:1 ME | 0.3 | 0.6 | 0 |
| C18:2 ME | 17.6 | 0.3 | 72.2 |
| C18:3 ME | 0.4 | 0 | 1.6 |
| Total, wt % | 100 | 100 | 100 |
| Normalized Amount, gms | 100 | 76 | 24 |

Example 3

Separation of Polyunsaturated Fatty Acid Esters

The post-distillation sample from Example 1 was treated using a simulated moving bed (SMB) chromatography. In this example, the SMB unit is set to operate on the principle of preferential adsorption of polyunsaturated fatty acid methyl esters relative to the saturated fatty acid methyl esters and the monounsaturated fatty acid methyl esters. The ORPHEUS adsorbent (Orochem Technologies Inc., Naperville, Ill., USA) was used as the adsorbent. Heptane (normal) was used as the desorbing solvent. In this mode of operation, the C18:2 unsaturated methyl esters and C18:3 unsaturated methyl esters were preferentially adsorbed in the first zone of the adsorbent bed. In the second zone, the saturated methyl esters and C18:1 unsaturated methyl esters were removed from the pores of the adsorbent by the n-heptane desorbent. In the third zone of the bed, C18:2 unsaturated methyl esters and the C18:3 unsaturated methyl esters were desorbed from the adsorbent by n-heptane. The mixture of the rejected portion of the feed (raffinate) and n-heptane was sent to a distillation column to recover and recycle the n-heptane desorbent and produce the raffinate stream containing primarily the saturated methyl esters and C18:1 unsaturated methyl esters and other monounsaturated methyl esters in the feed. The extract stream including a mixture of the C18:2 unsaturated methyl esters and C18:3 unsaturated methyl esters and n-heptane was sent to a distillation column. In the column, the n-heptane was recovered and recycled to the process. The extract product contained primarily the C18:2 unsaturated methyl esters and the C18:3 unsaturated methyl esters. In this instance, where the feed contained only about 20 wt % of these components, the SMB unit capital and operating costs tended to be about 50% smaller than if the process of Example 2 were performed on a feed of similar composition. Table 2, below, shows the results of the separation. The C18:1 unsaturated methyl ester recovery was 94% of the amount contained in the feed. The saturated methyl esters and C18:1 methyl ester purity in the SMB product was 99.5 wt %.

TABLE 2

| Composition (wt %) | Feed | SMB Product | SMB Reject |
| --- | --- | --- | --- |
| C16:0 ME | 3.4 | 3.5 | 3.1 |
| C18:0 ME | 8.3 | 9.9 | 3.4 |
| C20:0 ME | 0.8 | 0.2 | 2.7 |
| C16:1 ME | 0.1 | 0.1 | 0.1 |
| C18:1 ME | 69.1 | 85.7 | 17.3 |
| C20:1 ME | 0.3 | 0.2 | 0.6 |
| C18:2 ME | 17.6 | 0.5 | 71.2 |
| C18:3 ME | 0.4 | 0 | 1.7 |
| Total, wt % | 100 | 100 | 100 |
| Normalized Amount, gms | 100 | 76 | 24 |

What is claimed is:

1. A method of producing esters from a natural oil, comprising:
providing a natural oil feedstock comprising glycerides;
transesterifying the glycerides to provide a transesterified product comprising monounsaturated fatty acid esters and polyunsaturated fatty acid esters;
separating the polyunsaturated fatty acid esters from the monounsaturated fatty acid esters, to provide a separated monounsaturated fatty acid ester composition having a ratio of at least 10 parts by weight of monounsaturated fatty acid esters for every 1 part by weight of polyunsaturated fatty acid esters; and
metathesizing the separated monounsaturated fatty acid ester composition in the presence of a metathesis catalyst to provide a metathesized product comprising metathesized monounsaturated fatty acid esters and at least one olefin.

2. The method of claim 1, wherein the separating is conducted by a moving bed chromatographic separation, a crystallization separation, a membrane separation, a distillation separation, a salt solubility separation, an adsorption separation, a phase separation, an ionic liquid separation, a urea complexation separation, or a combination thereof.

3. The method of claim 1, wherein the separating is conducted by a moving bed chromatographic separation.

4. The method of claim 3, wherein the moving bed chromatographic separation includes use of an aqueous alcohol as an eluent.

5. The method of claim 4, wherein the aqueous alcohol is water and one or more short chain alcohols having 1 to 6 carbon atoms.

6. The method of claim 3, wherein the moving bed chromatographic separation includes use of an aqueous organic solvent as an eluent.

7. The method of claim 6, wherein the aqueous organic solvent is water and one or more ethers, esters, ketones, nitriles, or combinations thereof.

8. The method of claim 1, wherein the ratio is at least 20 parts by weight of monounsaturated fatty acid esters for every 1 part by weight of polyunsaturated fatty acid esters.

9. The method of claim 1, wherein the transesterified product further comprises saturated fatty acid esters and, prior to the metathesizing, separating the saturated fatty acid esters from the separated monounsaturated fatty acid ester composition.

10. The method of claim 9, wherein the separating further comprises providing a separated monounsaturated fatty acid ester composition, wherein the separated polyunsaturated fatty acid ester composition comprises less than 50 wt. % of the monounsaturated fatty acid esters and the saturated fatty acid esters from the natural oil feedstock, combined.

11. The method of claim 9, wherein the separating further comprises providing a separated polyunsaturated fatty acid ester composition, wherein the separated polyunsaturated fatty acid esters composition comprises at least 95 wt. % of the polyunsaturated fatty acid esters from the natural oil feedstock and less than 10 wt. % of the monounsaturated fatty acid esters and the saturated fatty acid esters from the natural oil feedstock, combined.

12. The method of claim 1, wherein the separated monounsaturated fatty acid esters composition comprise less than 5 wt. % polyunsaturated fatty acid esters.

13. The method of claim 1, wherein the metathesizing comprises a cross-metathesis reaction between the separated monounsaturated fatty acid esters and an olefin feedstock, to provide a metathesized product comprising metathesized olefins and metathesized monounsaturated fatty acid esters.

14. The method of claim 13, wherein the olefin feedstock comprises an alpha-olefin.

15. The method of claim 14, wherein the alpha-olefin is 1-butene.

16. The method of claim 15, wherein the metathesized monounsaturated fatty acid esters comprise 9-deconoic acid methyl ester and 9-dodecenoic acid methyl ester.

17. The method of claim 13, wherein the olefin feedstock comprises ethylene.

18. The method of claim 17, wherein the metathesized monounsaturated fatty acid esters comprise 9-deconoic acid methyl ester.

19. The method of claim 17, wherein at least 50 wt. % of the metathesized monounsaturated fatty acid esters in the metathesized product comprise 9-deconoic acid methyl ester.

20. The method of claim 13, further comprising separating the metathesized olefins from the metathesized monounsaturated fatty acid esters.

* * * * *